United States Patent
Sato et al.

(10) Patent No.: US 9,861,577 B2
(45) Date of Patent: Jan. 9, 2018

(54) ORALLY DISINTEGRATING TABLET

(75) Inventors: Takafumi Sato, Tokyo (JP); Motohiro Ota, Tokyo (JP); Makoto Kigoshi, Tokyo (JP); Hideki Morita, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 13/820,108

(22) PCT Filed: Aug. 31, 2011

(86) PCT No.: PCT/JP2011/069736
§ 371 (c)(1),
(2), (4) Date: May 14, 2013

(87) PCT Pub. No.: WO2012/029838
PCT Pub. Date: Mar. 8, 2012

(65) Prior Publication Data
US 2013/0274348 A1    Oct. 17, 2013

(30) Foreign Application Priority Data

Aug. 31, 2010 (JP) ................................ 2010-194755
Sep. 13, 2010 (JP) ................................ 2010-204758

(51) Int. Cl.
*A61K 9/00* (2006.01)
*A61K 9/20* (2006.01)
*A61K 31/454* (2006.01)

(52) U.S. Cl.
CPC .......... *A61K 9/0056* (2013.01); *A61K 9/2018* (2013.01); *A61K 9/2027* (2013.01); *A61K 31/454* (2013.01)

(58) Field of Classification Search
CPC .. A61K 9/0056; A61K 9/2027; A61K 31/454; A61K 9/2018
USPC ...................... 427/2.14; 514/772.4
See application file for complete search history.

(56) References Cited

U.S. PATENT DOCUMENTS

| | | | |
|---|---|---|---|
| 2004/0171669 A1 | 9/2004 | Chenevier | |
| 2007/0196494 A1 | 8/2007 | Grenier et al. | |
| 2007/0298103 A1* | 12/2007 | Hayes | 424/468 |
| 2008/0063706 A1* | 3/2008 | Tidmarsh et al. | 424/464 |
| 2008/0193544 A1 | 8/2008 | Bruck-Scheffler et al. | |
| 2008/0241237 A1 | 10/2008 | Venkatesh | |
| 2009/0148524 A1* | 6/2009 | Higuchi et al. | 424/470 |
| 2009/0311321 A1 | 12/2009 | Mimura et al. | |
| 2010/0136122 A1 | 6/2010 | Okochi et al. | |
| 2011/0229570 A1 | 9/2011 | Sugimoto et al. | |
| 2013/0115287 A1 | 5/2013 | Nakamura et al. | |

FOREIGN PATENT DOCUMENTS

| | | |
|---|---|---|
| EP | 2591774 A1 | 5/2013 |
| EP | 2 614 816 A1 * | 7/2013 |
| EP | 2614816 A1 | 7/2013 |
| JP | 2000044490 A | 2/2000 |
| JP | 2007-297348 A | 11/2007 |
| JP | 2009/114113 A | 5/2009 |
| JP | 2010/143836 A | 7/2010 |
| WO | 95/20380 A1 | 8/1995 |
| WO | 0048575 A1 | 8/2000 |
| WO | 2006/097456 A1 | 9/2006 |
| WO | 2008/119033 A1 | 10/2008 |
| WO | 2009/078034 A2 | 6/2009 |
| WO | WO-2010/061846 | 6/2010 |
| WO | 2012/029348 A1 | 3/2012 |

OTHER PUBLICATIONS

Eng. Translation of WO 2010061846 A.*
EUDRAGIT, an EVONIX product, May 2014.*
International Search Report and Written Opinion mailed Oct. 25, 2011, in corresponding PCT application No. PCT/JP2011/069736.

* cited by examiner

*Primary Examiner* — Blessing M Fubara
(74) *Attorney, Agent, or Firm* — Mintz Levin Cohn Ferris Glovsky and Popeo, P.C.

(57) ABSTRACT

It is an object of the present invention to provide an orally disintegrating tablet that has desirable oral disintegrability and excellent tablet hardness, a process for producing the same, and the like.

The present invention provides an orally disintegrating tablet comprising:
at least one diluent selected from D-mannitol, lactose, trehalose, xylitol, maltitol, and erythritol; a drug; a disintegrant; and
at least one binder selected form methacrylic acid copolymer S, methacrylic acid copolymer L, methacrylic acid-ethyl acrylate copolymer, ethyl acrylate-methyl methacrylate copolymer, and methyl methacrylate-butyl methacrylate-dimethylaminoethyl methacrylate copolymer.

11 Claims, No Drawings

ORALLY DISINTEGRATING TABLET

CROSS-REFERENCE TO RELATED APPLICATIONS

This application is the U.S. national phase application, pursuant to 35 U.S.C. §371, of PCT/JP2011/069736, filed Aug. 31, 2011, designating the United States, which claims priority to Japanese Application Nos. 2010-204758, filed Sep. 13, 2010, and 2010-194755, filed Aug. 31, 2010. The entire contents of each of the aforementioned patent applications are incorporated herein by this reference.

TECHNICAL FIELD

The present invention relates to orally disintegrating tablets, processes for producing the same, and the like.

BACKGROUND ART

Taking oral solid medical drug products such as usual tablets and capsules can be problematic for the elderly having a weakened ability to swallow. The same problem is presented also for children with a low swallowing ability. As a dosage form suited for the elderly and children, there is a recent demand for the development of orally disintegrating tablets that quickly dissolve or disintegrate in the mouth.

However, efforts to make a tablet quickly disintegrable in the mouth generally result in lowered tablet hardness. Low tablet hardness may cause tablet cracking, for example, during the manufacture or packaging process or during the distribution, or when taking the tablet out of a packaging container, with the result that the commodity values decrease. Satisfying both of the oral disintegrability and tablet hardness at the same time is indeed an important factor in orally disintegrating tablets.

As a rule, tablet disintegrability and hardness are contradictory, meaning that efforts to improve hardness may lower tablet disintegrability. Further, the disintegrability of common tablets, and the oral disintegrability of orally disintegrating tablets are similar but different concepts. A measure that successfully satisfies both of disintegrability and tablet hardness in common tablets cannot easily satisfy both of the oral disintegrability and tablet hardness of orally disintegrating tablets.

There have been attempts to satisfy both of the oral disintegrability and tablet hardness of orally disintegrating tablets, as described in, for example, Patent Documents 1 and 2. Patent Document 1 describes a method of compression molding a granule obtained by granulating a poorly moldable sugar with a readily moldable sugar. Patent Document 2 describes a tablet obtained by compression molding a granulated material obtained by binding a mixed powder of a principal agent, an easily wettable sugar, and a disintegrant with a binder that contains an easily wettable sugar.

Patent Document 3 describes that a certain type of acrylic polymer, that is USP/NF methacrylic acid copolymer C can significantly increase the tablet disintegration rate, and can produce a tablet having highly desirable pharmaceutical characteristics, particularly excellent cohesion.

CITATION LIST

Patent Documents

Patent Document 1: WO95/020380
Patent Document 2: WO00/048575
Patent Document 3: Japanese Published Unexamined Patent Application No. 2000-044490

SUMMARY OF THE INVENTION

Problems to be Solved by the Invention

It is an object of the present invention to provide an orally disintegrating tablet that has desirable oral disintegrability and excellent tablet hardness, a process for producing the same, and the like.

Means for Solving the Problems

The present invention relates to the following (1) to (14).

(1) An orally disintegrating tablet comprising:
at least one diluent selected from D-mannitol, lactose, trehalose, xylitol, maltitol, and erythritol; a drug; a disintegrant; and
at least one binder selected form methacrylic acid copolymer S, methacrylic acid copolymer L, methacrylic acid-ethyl acrylate copolymer, ethyl acrylate-methyl methacrylate copolymer, and methyl methacrylate-butyl methacrylate-dimethylaminoethyl methacrylate copolymer.

(2) The orally disintegrating tablet according to the above (1), wherein the binder is at least one binder selected from methacrylic acid copolymer S and methacrylic acid copolymer L, and contains triethyl citrate in 30 to 100 weight % based on the binder.

(3) The orally disintegrating tablet according to the above (1), wherein the binder contains at least one binder selected from JPE dry methacrylic acid copolymer LD and a copolymer resin of methacrylic acid and ethyl acrylate in JPE methacrylic acid copolymer LD; a copolymer resin of ethyl acrylate and methyl methacrylate in a JPE ethyl acrylate-methyl methacrylate copolymer dispersion; and JPE aminoacrylmethacrylate copolymer E.

(4) The orally disintegrating tablet according to any one of the above (1) to (3), wherein the weight ratio of the diluent to the binder is 100:1 to 4:1.

(5) The orally disintegrating tablet according to any one of the above (1) to (4), wherein the disintegrant is at least one disintegrant selected from crospovidone, low-substituted hydroxypropylcellulose, crosscarmellose sodium, and starch.

(6) The orally disintegrating tablet according to any one of the above (1) to (5), wherein the orally disintegrating tablet has a tablet hardness of 40 to 100 N.

(7) The orally disintegrating tablet according to any one of the above (1) to (6), further comprising a water-soluble film coating layer on a tablet surface.

(8) A process for producing an orally disintegrating tablet that contains at least one diluent selected from D-mannitol, lactose, trehalose, xylitol, maltitol, and erythritol; a drug; and a disintegrant, the process comprising steps of:

adding a binder liquid to the diluent and performing wet granulation, the binder liquid containing at least one binder selected from methacrylic acid copolymer S, methacrylic acid copolymer L, methacrylic acid-ethyl acrylate copolymer, ethyl acrylate-methyl methacrylate copolymer, and methyl methacrylate-butyl methacrylate-dimethylaminoethyl methacrylate copolymer; and tableting the granulated material.

(9) The process according to the above (8), wherein the binder liquid is at least one binder liquid selected from:

(a) an organic solvent liquid in which at least one binder selected from methacrylic acid copolymer S, methacrylic acid copolymer L, and ethyl acrylate-methyl methacrylate copolymer dissolves;

(b) a liquid obtained by suspending at least one binder selected from methacrylic acid copolymer S and methacrylic acid copolymer L in an aqueous solution in which triethyl citrate dissolves in 30 to 100 weight % based on the binder;

(c) a liquid obtained by suspending JPE dry methacrylic acid copolymer LD and/or JPE aminoacrylmethacrylate copolymer E in water; and (d) a JPE methacrylic acid copolymer LD and/or a JPE ethyl acrylate-methyl methacrylate copolymer dispersion.

(10) The process according to the above (8) or (9), wherein the wet granulation is fluidized bed granulation.

(11) The process according to any one of the above (8) to (10), wherein the weight ratio of the diluent to the binder in the wet granulation step is 100:1 to 4:1.

(12) The process according to any one of the above (8) to (11), wherein the disintegrant is at least one disintegrant selected from crospovidone, low-substituted hydroxypropylcellulose, crosscarmellose sodium, and starch.

(13) The process according to any one of the above (8) to (12), wherein the punch pressure in the tableting step produces a tablet hardness of 40 to 100 N.

(14) The process according to any one of the above (8) to (13), further comprising a step of coating a water-soluble film on the tablet obtained in the tableting step.

Effect of the Invention

The present invention can provide an orally disintegrating tablet that has desirable oral disintegrability and excellent tablet hardness.

MODE FOR CARRYING OUT THE INVENTION

The orally disintegrating tablet of the present invention contains: at least one diluent selected from D-mannitol, lactose, trehalose, xylitol, maltitol, and erythritol; a drug; a disintegrant; and at least one binder selected from methacrylic acid copolymer S, methacrylic acid copolymer L, methacrylic acid-ethyl acrylate copolymer, ethyl acrylate-methyl methacrylate copolymer, and methyl methacrylate-butyl methacrylate-dimethylaminoethyl methacrylate copolymer.

In the present invention, examples of the D-mannitol, lactose, trehalose, xylitol, maltitol, and erythritol include those described in, for example, Japanese Pharmacopoeia (JP) or Japanese Pharmaceutical Excipients (JPE). These are also inclusive of hydrates (for example, lactose hydrate, and the like).

The orally disintegrating tablet of the present invention preferably contains at least one diluent selected from D-mannitol, lactose, trehalose, xylitol, maltitol, and erythritol, preferably at least one diluent selected from D-mannitol, lactose, and erythritol, more preferably D-mannitol in 20 to 95 weight %, more preferably 40 to 90 weight %, further preferably 60 to 85 weight %.

The volume average particle diameter of at least one diluent selected from D-mannitol, lactose, trehalose, xylitol, maltitol, and erythritol is preferably 5 to 150 μm, more preferably 10 to 100 μm, further preferably 15 to 60 μm. In the present invention, volume average particle diameter may be determined by calculation, for example, by measuring the unidirectional particle diameters by microscopy or by using a laser method and regarding the measured values as spherical particle diameters.

In the present invention, examples of the methacrylic acid copolymer S and methacrylic acid copolymer L may be those described in, for example, JP or JPE.

As used herein, the methacrylic acid-ethyl acrylate copolymer is a copolymer resin of methacrylic acid and ethyl acrylate. Examples thereof include JPE dry methacrylic acid copolymer LD (Eudragit L100-55 (Roehm Pharma Gmbh) and the like), copolymer resin of methacrylic acid and ethyl acrylate in JPE methacrylic acid copolymer LD (Eudragit L30D-55 (Roehm Pharma Gmbh) and the like).

In the present invention, the ethyl acrylate-methyl methacrylate copolymer is a copolymer resin of ethyl acrylate and methyl methacrylate. Examples thereof include copolymer resin of ethyl acrylate and methyl methacrylate in JPE ethyl acrylate-methyl methacrylate copolymer dispersion (Eudragit NE30D (Roehm Pharma Gmbh) and the like), and the like.

In the present invention, the methyl methacrylate-butyl methacrylate-dimethylaminoethyl methacrylate copolymer is a copolymer resin of methyl methacrylate, butyl methacrylate, and dimethylaminoethyl methacrylate. Examples thereof include JPE aminoacrylmethacrylate copolymer E (Eudragit E (Roehm Pharma Gmbh), Eudragit EPO (Roehm Pharma Gmbh) and the like), copolymer resin of methyl methacrylate, butyl methacrylate, and dimethylaminoethyl methacrylate in an aminoacrylmethacrylate copolymer E dispersion (Eudragit E30D (Roehm Pharma Gmbh) and the like), and the like.

The orally disintegrating tablet of the present invention preferably contains at least one binder selected from methacrylic acid copolymer S, methacrylic acid copolymer L, methacrylic acid-ethyl acrylate copolymer, ethyl acrylate-methyl methacrylate copolymer, and methyl methacrylate-butyl methacrylate-dimethylaminoethyl methacrylate copolymer, preferably at least one binder selected from JPE dry methacrylic acid copolymer LD, and copolymer resin of methacrylic acid and ethyl acrylate in JPE methacrylic acid copolymer LD, copolymer resin of ethyl acrylate and methyl methacrylate in JPE ethyl acrylate-methyl methacrylate copolymer dispersion, and JPE aminoacrylmethacrylate copolymer E in 0.01 to 50 weight %, more preferably 0.1 to 20 weight %, further preferably 1 to 10 weight % of the orally disintegrating tablet.

When the binder is at least one binder selected from methacrylic acid copolymer S and methacrylic acid copolymer L, the orally disintegrating tablet of the present invention preferably further contains triethyl citrate in 30 to 100 weight %, preferably 40 to 80 weight % based on the binder.

In the orally disintegrating tablet of the present invention, the diluent-to-binder weight ratio is preferably 100:1 to 4:1, more preferably 50:1 to 85:15, further preferably 25:1 to 9:1.

The drug used in the present invention is not limited, as long as it can be orally administered as a drug in an orally disintegrating tablet. Examples thereof include one or more components selected from antipyretic analgesic antiphlogistics, psychotropics, antianxiety drugs, antidepressants, hypnotics, anticonvulsants, CNS-acting drugs, brain metabolism ameliorant, cerebral circulation ameliorants, antiepileptic drugs, sympathomimetic drugs, gastrointestinal drugs, acid suppressants, anti-ulcerogenic drugs, cough medicines, antiemetics, anapnoics, bronchodilators, allergy drugs, dental and oral agents, antihistamine agents, cardiants, cardiac arrhythmia agents, diuretics, depressors, vasoconstrictors, coronary vasodilators, peripheral vasodilators, hyperlipidemias agents, cholagogues, antibiotics, chemotherapy agents, diabetes agents, osteoporosis agents, antirheumatic drugs, antispasmodics, hormonal agents, alkaloidal narcotics, sulfa drugs, gout remedies, anticoagulants, antineoplastics, nutrient and tonic agents with health claims, and the like.

Specific examples of the drug used in the present invention include cinacalcet, topiramate, olopatadine, and the like, and pharmaceutically acceptable salts thereof, and the like.

When the drug used in the present invention is a pharmaceutically acceptable salt, the pharmaceutically acceptable salt is inclusive of, for example, pharmaceutically acceptable acid addition salts, metal salts, ammonium salts, organic amine addition salts, amino acid addition salts, and the like. Examples of the pharmaceutically acceptable acid addition salts include inorganic acid salts, for example, such as hydrochloride, hydrobromate, nitrate, sulfate, and phosphate, and organic acid salts, for example, such as acetate, maleate, fumarate, tartrate, and citrate. Examples of the pharmaceutically acceptable metal salts include alkali metal salts, for example, such as lithium salts, sodium salts, and potassium salts, and alkaline-earth metal salts (for example, such as magnesium salts, and calcium salts), aluminum salts, and zinc salts. Examples of the pharmaceutically acceptable ammonium salts include salts of, for example, ammonium, tetramethylammonium, and the like. Examples of the pharmaceutically acceptable organic amine addition salts include addition salts of, for example, morpholine, piperidine, and the like. Examples of the pharmaceutically acceptable amino acid addition salts include addition salts of, for example, lysine, glycine, phenylalanine, aspartic acid, glutamic acid, and the like.

The orally disintegrating tablet of the present invention contains the drug in preferably 0.5 to 80 weight %, more preferably 1 to 50 weight %, further preferably 2 to 30 weight %, most preferably 5 to 20 weight % of the orally disintegrating tablet. Further, the drug has a volume average particle diameter of preferably 2 to 150 μm, more preferably 5 to 100 μm, further preferably 15 to 50 μm. In the present invention, volume average particle diameter may be determined by calculation, for example, by measuring the unidirectional particle diameters by using, for example, a laser method and regarding the measured values as spherical particle diameters, specifically, by using a Mastersizer 2000 (Malvern) with ethanol used as the dispersion medium.

The drug in the orally disintegrating tablet of the present invention may be in the form of a drug-containing granule. The drug-containing granule has a weight average particle diameter of preferably 75 to 850 μm, more preferably 100 to 500 μm, further preferably 125 to 300 μm as measured by sieving. In the present invention, weight average particle diameter may be determined by, for example, sieving.

Examples of the disintegrant used in the present invention include cellulose derivatives (for example, crosscarmellose sodium, carmellose sodium, carmellose potassium, carmellose calcium, low-substituted hydroxypropylcellulose, and the like), starches (for example, corn starch, potato starch, rice starch, wheat starch, pregelatinated starch, partially pregelatinated starch, and the like), starch derivatives (carboxymethyl starch sodium, hydroxypropyl starch, and the like), crospovidone, bentonite, and the like. These may be used either alone or in combinations of two or more. Further, for desirable productivity and/or quick drug solubility, it is preferable to contain at least one disintegrant selected from crospovidone, low-substituted hydroxypropylcellulose, crosscarmellose sodium, hydroxypropyl starch, starch, and the like, more preferably at least one disintegrant selected from crospovidone, low-substituted hydroxypropylcellulose, crosscarmellose sodium, and starch, further preferably crospovidone. Note that the disintegrant may also serve as, for example, an diluent and/or a binder, and the like.

The orally disintegrating tablet of the present invention preferably contains a disintegrant, preferably at least one disintegrant selected from crospovidone, low-substituted hydroxypropylcellulose, crosscarmellose sodium, hydroxypropyl starch, starch, and the like, more preferably at least one disintegrant selected from crospovidone, low-substituted hydroxypropylcellulose, crosscarmellose sodium, and starch, further preferably crospovidone in 1 to 30 weight %, more preferably 2 to 25 weight %, further preferably 3 to 15 weight %.

The orally disintegrating tablet of the present invention may contain other active components and/or other excipients, in addition to at least one diluent selected from D-mannitol, lactose, trehalose, xylitol, maltitol, and erythritol; a drug; a disintegrant; and at least one binder selected from methacrylic acid copolymer S, methacrylic acid copolymer L, methacrylic acid-ethyl acrylate copolymer, ethyl acrylate-methyl methacrylate copolymer, and methyl methacrylate-butyl methacrylate-dimethylaminoethyl methacrylate copolymer.

Examples of other excipients include those used for, for example, diluents, binders, lubricants, and the like in common solid preparations.

Examples of the diluents as other excipients include sugars (for example, sucrose, maltose, and the like), sugar alcohols (for example, sorbitol, and the like), celluloses (for example, microcrystalline cellulose, powder cellulose, and the like), poorly water-soluble inorganic salts (for example, talc, light anhydrous silicic acid, and the like), and the like. These may be used either alone or in combinations of two or more.

Examples of the binders as other excipients include cellulose derivatives (for example, methyl cellulose, carmellose, carboxypropylcellulose, hydroxypropylcellulose, hydroxypropyl methylcellulose, and the like), celluloses (for example, crystalline cellulose, and the like), starches (for example, pregelatinated starch, and the like), polyvinyl alcohols, polyvinyl pyrrolidones, pullulans, dextrins, gum arabic, gelatin, and the like. These may be used either alone or in combinations of two or more.

Examples of the lubricants as other excipients include, for example, magnesium stearate, calcium stearate, sodium stearyl fumarate, hardened oil, sucrose fatty acid ester, polyethylene glycol, and the like. More preferred examples include magnesium stearate, calcium stearate, sodium stearyl fumarate, and the like. These may be used either alone or in combinations of two or more.

The orally disintegrating tablet of the present invention may also contain dyes, light-shielding agents, and flavoring ingredients. Examples thereof include titanium oxides, iron oxides (specifically, yellow ferric oxide, ferric oxide, yellow iron oxide, black iron oxide, and the like), zinc oxides, silicon oxides, red iron oxide, carbon blacks, medicinal carbon, barium sulfate, food yellow 4 aluminum lake, food red 2, food red 3, food red 102, copper chlorophin, and various other flavoring ingredients, and the like.

In the present invention, the orally disintegrating tablet is preferably, for example, circle-shaped, triangular-shaped, ball-shaped, and the like. The size of the tablet of the present invention is not particularly limited, and is, for example, preferably 0.1 to 1 g in mass, and 0.5 to 1.5 cm in diameter.

In the present invention, the orally disintegrating tablet preferably has excellent hardness that does not cause, for example, chipping, breaking, and the like, preferably hardness that does not cause chipping, breaking, and the like in the packaging step that uses an automatic tablet packing machine, more preferably hardness that does not cause chipping, breaking, and the like also in the coating step of forming a water-soluble film coating layer on the tablet surface. The tablet hardness is generally measured as the break strength of the tablet in diametrical direction, using a tablet hardness meter. The value of tablet harness is preferably 40 to 200 N, more preferably 50 to 150 N, particularly preferably 60 to 100N. The tablet hardness may be measured by using a commercially available tablet break strength measurement device, for example, a PTB-311E available from Japan Machinery Company.

In the present invention, the disintegration time of the orally disintegrating tablet in the mouth is preferably 1 minute or less, more preferably 30 seconds or less. For example, the time for a dye solution to completely infiltrate a tablet surface (absorption time) is preferably 1 minute or less, more preferably 30 seconds or less as measured by the absorption time measurement method (see Hisakazu Sunada, Chem. Pharm. Bull), 1996, Vol. 44, No. 11, p. 2121-2127), an in vitro test that simulates oral disintegration time.

The process for producing the orally disintegrating tablet of the present invention is a process for producing an orally disintegrating tablet that contains at least one diluent selected from D-mannitol, lactose, trehalose, xylitol, maltitol, and erythritol; a drug; and a disintegrant. For example, the process may include the step of adding a binder liquid to the diluent and performing wet granulation, and the step of tableting the resulting granulated material.

Examples of the methods used to add a binder liquid to the diluent and perform wet granulation include an extrusion granulation method (using a screw extrusion granulation device, a roller extrusion granulation device, and the like), a tumbling granulation method (using a rotary drum granulation device, a centrifugal tumbling granulation device, and the like), a fluidized bed granulation method (using a fluidized bed granulation and drying device, a tumbling fluidized bed granulation device, and the like), a stirring granulation method (using a stirring granulation device, and the like), and the like. Preferred examples include a fluidized bed granulation method, a stirring granulation method, and the like. More preferred examples include a fluidized bed granulation method. In any case, it is preferable to add the binder liquid and perform granulation, and dry the resulting granulated material. Preferably, the binder liquid is added by spraying.

In the present invention, the fluidized bed granulation method is the granulation method in which a binder liquid is sprayed while flowing powder particles with heated air sent from a lower portion of a granulator. The method is also inclusive of, for example, the counter spray method in which the binder liquid is sprayed from the top, and the parallel method (Wurster method) in which the binder liquid is sprayed from the bottom. The method also encompasses the tumbling fluidized bed granulation method that involves rotation of the bottom portion of a granulator container.

In the wet granulation performed with the binder liquid added to the diluent, the wet granulation may be performed by adding the binder liquid after mixing the diluent with the drug and/or the disintegrant, and, as desired, other active components and/or other excipients.

Examples of the binder liquid include solutions and dispersions prepared by dissolving or dispersing at least one binder selected from methacrylic acid copolymer S, methacrylic acid copolymer L, methacrylic acid-ethyl acrylate copolymer, ethyl acrylate-methyl methacrylate copolymer, and methyl methacrylate-butyl methacrylate-dimethylaminoethyl methacrylate copolymer in, for example, organic solvents (such as ethanol, isopropyl alcohol, and acetone), water, or mixed solvents thereof, or mixed solvents of these with methylene chloride, and the like.

Preferred are one or more binder liquids selected from (a) organic solvent liquids in which at least one binder selected from methacrylic acid copolymer S, methacrylic acid copolymer L, and ethyl acrylate-methyl methacrylate copolymer dissolves, (b) liquids obtained by suspending at least one binder selected from methacrylic acid copolymer S and methacrylic acid copolymer L in an aqueous solution in which triethyl citrate dissolves in 30 to 100 weight % of based on the binder, (c) liquids obtained by suspending JPE dry methacrylic acid copolymer LD and/or JPE aminoacrylmethacrylate copolymer E in water, and (d) JPE methacrylic acid copolymer LD and/or JPE ethyl acrylate-methyl methacrylate copolymer dispersion.

More preferred are one or more binder liquids selected from (c) liquids obtained by suspending JPE dry methacrylic acid copolymer LD and/or JPE aminoacrylmethacrylate copolymer E in water, and (d) JPE methacrylic acid copolymer LD and/or JPE ethyl acrylate-methyl methacrylate copolymer dispersion.

Further preferred are liquids obtained by suspending JPE dry methacrylic acid copolymer LD in water, and JPE methacrylic acid copolymer LD.

Note that the organic solvent liquid is a liquid that contains a solvent other than water as a main component, preferably a liquid that does not contain substantially any water. The aqueous solution is a liquid that contains water as a main component, preferably a liquid that does not contain substantially any other solvent aside from water.

The binder is contained in the binder liquid in amounts that make the diluent-to-binder weight ratio in the wet granulation step preferably 100:1 to 4:1, more preferably 50:1 to 85:15, further preferably 25:1 to 9:1.

The binder liquid may contain a plasticizer or a lubricant for purposes including improving the handing and ease of granulation in the granulation procedures, and the like.

Further, drugs (having the same definitions as described above) or disintegrants (having the same definitions as described above) may be contained in the binder liquid, as desired. Dissolving and mixing a poorly soluble drug in the binder liquid advantageously improves the drug solubility (absorbability in the digestive tract) of the product orally disintegrating tablet as the binder forms a solid dispersion with the poorly soluble drug.

Examples of the plasticizers that can be contained in the binder liquid include triethyl citrate, polyethylene glycol, triacetin, propylene glycol, and the like. Generally, the plasticizer is contained in 1 to 30 weight %, preferably 5 to 20 weight % based on the binder in the binder liquid. However, when the binder liquid is one obtained by suspending at least one selected from methacrylic acid copolymer S and methacrylic acid copolymer L in an aqueous solution, triethyl citrate is contained as the plasticizer in 30 to 100 weight %, preferably 40 to 80 weight % based on the binder in the binder liquid.

Examples of the lubricants that can be contained in the binder liquid include talc, stearic acid, light anhydrous silicic acid, hydrous silicon dioxide, calcium silicate, and the like. The lubricant is contained in 1 to 30%, preferably 5 to 25%, further preferably 10 to 20 weight % based on the binder in the binder liquid. However, when the binder liquid is one obtained by suspending at least one binder selected from methacrylic acid copolymer S and methacrylic acid copolymer L in an aqueous solution, the lubricant is preferably contained in 30 to 100 weight %, preferably 40 to 80 weight % based on the binder in the binder liquid.

The binder liquid may also contain D-mannitol, lactose, trehalose, xylitol, maltitol, erythritol, and the like. The amounts of D-mannitol, lactose, trehalose, xylitol, maltitol, erythritol, and the like are 2 to 20 weight %, preferably 3 to 10 weight % based on the binder in the binder liquid.

The orally disintegrating tablet of the present invention may be produced by tableting the granulated material with a tableting machine. When the granulated material does not contain a drug and/or a disintegrant, the orally disintegrating tablet may be produced by mixing the drug and/or disintegrant with the granulated material and tableting the obtained mixture with a tableting machine. In any case, the orally disintegrating tablet may be produced by further mixing, as desired, at least one diluent selected from lactose, trehalose, xylitol, maltitol, and erythritol; a drug (having the same definition as described above); a disintegrant (having the same definition as described above); and/or other excipients (having the same definition as described above) and tableting the obtained mixture with a tableting machine.

The tableting machine that can be used in the present invention is not particularly limited, and, for example, a rotary tableting machine, a hydraulic press, and the like may be used. It is also possible to use, for example, a tableting machine equipped with punches and dies to which very trace amounts of lubricants such as stearic acid, metal salts thereof (such as magnesium stearate, calcium stearate, and the like), sucrose fatty acid ester, glycerin fatty acid ester, hydrogenated oil and fat, and the like have been applied, thereby producing the orally disintegrating tablet by so-called external lubrication tableting.

The punch pressure in the tableting step may be that that makes the tablet hardness 40 to 200 N, preferably 50 to 150 N, more preferably 60 to 100 N. For example, the punch pressure is 500 to 3,000 kgf/cm$^2$, preferably 800 to 2,500 kgf/cm$^2$, more preferably 1,000 to 2,000 kgf/cm$^2$.

The present invention is described below more specifically with reference to examples and test examples. It should be noted that the present invention is not limited by the following examples and test examples.

Example 1

333 g of JPE methacrylic acid copolymer LD (here and below, Eudragit L30D-55; Roehm Pharma Gmbh) (solid content, 100 g), 10 g of polyethylene glycol (here and below, PEG 6000; NOF Corporation), 10 g of talc (here and below, Kihara Kasei), and 400 g of purified water were mixed to obtain a binder liquid.

1,880 g of D-mannitol (here and below, Nikken Chemical and Synthetic Industry; volume average particle diameter of about 50 μm) was charged into a fluidized bed granulation drier (here and below, FLO-2; Freund), and the binder liquid was sprayed to form granules, followed by drying.

The resulting granulated material (198 g) was mixed with 2 g of magnesium stearate (here and below, Merck), and the mixture was punched with a rotary tableting machine (here and below, Kikusui Seisakusho; Collect Type-12; φ=8 mm; flat punch) to obtain orally disintegrating tablets.

Example 2

333 g of JPE ethyl acrylate-methyl methacrylate copolymer dispersion (here and below, Eudragit NE30D; Roehm Pharma Gmbh) (solid content, 100 g), polyethylene glycol (10 g), talc (10 g), and purified water (400 g) were mixed to obtain a binder liquid.

D-mannitol (1,880 g) was charged into a fluidized bed granulation drier, and the binder liquid was sprayed to form granules, followed by drying.

The resulting granulated material (198 g) was mixed with magnesium stearate (2 g), and the mixture was punched with a rotary tableting machine to obtain orally disintegrating tablets.

Comparative Example 1

D-mannitol (2,000 g) was charged into a fluidized bed granulation drier, and purified water (400 g) was sprayed to form granules, followed by drying.

The resulting granulated material (198 g) was mixed with magnesium stearate (2 g), and the mixture was punched with a rotary tableting machine to obtain orally disintegrating tablets.

Test Example 1

The tablets obtained in Examples 1 and 2 and Comparative Example 1 were measured for tablet hardness using a tablet hardness measurement device (PTB-311E; Japan Machinery Company). The measurement results are presented in Table 1.

TABLE 1

| | Component | Example 1 | Example 2 | Comparative Example 1 |
|---|---|---|---|---|
| Examination formulation (mg/tab) | D-mannitol | 186 | 186 | 198 |
| | Eudragit L30D-55 | 10 | — | — |
| | PEG6000 | 1 | 1 | — |
| | Talc | 1 | 1 | — |
| | Eudragit NE30D | — | 10 | — |
| | Magnesium stearate | 2 | 2 | 2 |
| | Total | 200 | 200 | 200 |
| Tablet hardness (N) | Tabletting pressure 600 kg | 67 | 42 | 15 |
| | 800 kg | 92 | 53 | 15 |
| | 1000 kg | 107 | 59 | 18 |

Example 3

A binder liquid was obtained in the same manner as in Example 1.

Lactose (Meggle; 1,880 g) was charged into a fluidized bed granulation drier, and the binder liquid was sprayed to form granules, followed by drying.

The resulting granulated material (198 g) was mixed with magnesium stearate (2 g), and the mixture was punched with a rotary tableting machine to obtain orally disintegrating tablets.

Comparative Example 2

Lactose (Meggle; 2,000 g) was charged into a fluidized bed granulation drier, and purified water (600 g) was sprayed to form granules, followed by drying.

The resulting granulated material (198 g) was mixed with magnesium stearate (2 g), and mixture was punched with a rotary tableting machine to obtain orally disintegrating tablets.

Test Example 2

The tablets obtained in Example 3 and Comparative Example 2 were measured for tablet hardness in the same manner as in Test Example 1. The measurement results are presented in Table 2.

TABLE 2

| | Component | Example 3 | Comparative Example 3 |
|---|---|---|---|
| Examination formulation (mg/tab) | Lactose | 186 | 198 |
| | Eudragit L30D-55 | 10 | — |
| | PEG6000 | 1 | — |
| | Talc | 1 | — |
| | Magnesium stearate | 2 | 2 |
| | Total | 200 | 200 |
| Tablet hardness (N) | Tabletting pressure 600 kg | 50 | 18 |
| | 800 kg | 75 | 26 |
| | 1000 kg | 88 | 34 |

Example 4

A binder liquid was obtained in the same manner as in Example 1.

1,880 g of erythritol (here and below, Nikken Chemical and Synthetic Industry) was charged into a fluidized bed granulation drier, and the binder liquid was sprayed to form granulates, followed by drying.

The resulting granulated material (198 g) was mixed with magnesium stearate (2 g), and the mixture was punched with a rotary tableting machine to obtain orally disintegrating tablets.

Comparative Example 3

Erythritol (2,000 g) was charged into a fluidized bed granulation drier, and purified water (400 g) was sprayed to form granulates, followed by drying.

The resulting granulated material (198 g) was mixed with magnesium stearate (2 g), and the mixture was punched with a rotary tableting machine to obtain orally disintegrating tablets.

Test Example 3

The tablets obtained in Example 4 and Comparative Example 3 were measured for tablet hardness in the same manner as in Test Example 1. The measurement results are presented in Table 3.

TABLE 3

| | Component | Example 4 | Comparative Example 4 |
|---|---|---|---|
| Examination formulation (mg/tab) | Erythritol | 186 | 198 |
| | Eudragit L30D-55 | 10 | — |
| | PEG6000 | 1 | — |
| | Talc | 1 | — |
| | Magnesium stearate | 2 | 2 |
| | Total | 200 | 200 |
| Tablet hardness (N) | Tabletting pressure 600 kg | 58 | unavailable moulding |
| | 800 kg | 77 | unavailable moulding |
| | 1000 kg | 88 | unavailable moulding |
| | 1200 kg | 100 | unavailable moulding |

Example 5

A binder liquid was obtained in the same manner as in Example 1.

50 g of domperidone (JP domperidone), and 1,720 g of D-mannitol were charged into a fluidized bed granulator, and the binder liquid was sprayed to form granules, followed by drying. The resulting dried material was sieved through a sieve having 710 μm openings to obtain a granulated material.

The granulated material (188 g) was mixed with 10 g of crospovidone (here and below, Polyplasdone XL-10; IPS) and 2 g of magnesium stearate, and the mixture was punched with a rotary tableting machine under the pressure that makes the tablet hardness about 60 N. As a result, orally disintegrating tablets were obtained.

Example 6

The granulated material (188 g) obtained in Example 5 was mixed with 10 g of low-substituted hydroxypropylcellulose (L-HPC LH-31, Shinetsu Chemical) and 2 g of magnesium stearate, and the mixture was punched with a rotary tableting machine under the pressure that makes the tablet hardness about 60 N. As a result, orally disintegrating tablets were obtained.

Example 7

The dry granulated material (188 g) obtained in Example 5 was mixed with 10 g of crosscarmellose sodium (FMC) and 2 g of magnesium stearate, and the mixture was punched with a rotary tableting machine under the pressure that makes the tablet hardness about 60 N. As a result, orally disintegrating tablets were obtained.

Example 8

The granulated material (188 g) obtained in Example 5 was mixed with 10 g of corn starch (Japan Corn Starch) and 2 g of magnesium stearate, and the mixture was punched with a rotary tableting machine under the pressure that makes the tablet hardness about 60 N. As a result, orally disintegrating tablets were obtained.

Comparative Example 4

Domperidone (50 g) and D-mannitol (1,720 g) were charged into a fluidized bed granulator, and purified water was sprayed to form granules, followed by drying. The resulting dried material was sieved through a sieve having 710 μm openings to obtain a granulated material.

The granulated material (188 g) was mixed with crospovidone (10 g) and magnesium stearate (2 g), and the mixture was punched with a rotary tableting machine under the punch pressure of 1,200 kg to obtain orally disintegrating tablets.

Test Example 4

The tablets obtained in Examples 5 to 8 and Comparative Example 4 were measured for tablet hardness in the same manner as in Test Example 1. The tablets were also measured for absorption time to evaluate disintegrability. The measurement results are presented in Tables 4 and 5.

Absorption Time Measurement

An aqueous solution (2 mL) of 10 mg/mL yellow 5 was dropped onto a circular filter paper having a diameter of 55 mm. One of the orally disintegrating tablets was then placed on the wetted filter paper, and the time required for the dye solution to completely infiltrate the tablet surface was measured.

TABLE 4

|  | Example 5 | Example 6 | Example 7 | Example 8 |
|---|---|---|---|---|
| Domperidone | 5 | 5 | 5 | 5 |
| D-mannitol | 171 | 171 | 171 | 171 |
| Eudragit L30D-55 | 10 | 10 | 10 | 10 |
| PEG6000 | 1 | 1 | 1 | 1 |
| Talc | 1 | 1 | 1 | 1 |
| Crospovidone | 10 | — | — | — |
| Low-substituted hydroxypropylcellulose | — | 10 | — | — |
| Crosscarmellose sodium | — | — | 10 | — |
| Corn starch | — | — | — | 10 |
| Magnesium stearate | 2 | 2 | 2 | 2 |
| Total (mg/tab) | 200 | 200 | 200 | 200 |
| Tablet hardness | 60N | 60N | 55N | 58N |
| Absorption Time | 16 sec | 32 sec | 42 sec | 45 sec |

TABLE 5

| Component and test item | Comparative Example 5 |
|---|---|
| Domperidone | 5 |
| D-mannitol | 183 |
| Crospovidone | 10 |
| Magnesium stearate | 2 |
| Total (mg/tab) | 200 |
| Tablet hardness | 22N |
| Absorption Time | 12 sec |

Example 9

A binder liquid was obtained by mixing 15 g of JPE aminoacrylmethacrylate copolymer E (Eudragit EPO; Roehm Pharma Gmbh), 1.5 g of sodium lauryl sulfate (nacalai tesque), stearic acid (2.25 g), talc (7.5 g), and purified water (146.2 g).

Domperidone (7.5 g), D-mannitol (248.3 g), and crospovidone (15.0 g) were charged into a fluidized bed granulator, and the binder liquid was sprayed to form granules, followed by drying. The resulting dried material was sieved through a sieve having 710 μm openings to obtain a granulated material.

The granulated material (206 g) was mixed with magnesium stearate (2.1 g), and the mixture was punched with a rotary tableting machine under the pressure that makes the tablet hardness about 80 N. As a result, orally disintegrating tablets were obtained.

Example 10

A binder liquid was obtained by mixing 15 g of JPE methacrylic acid copolymer L (here and below, Eudragit L100; Roehm Pharma Gmbh), 8.4 g of 1 N ammonium water, 7.5 g of triethyl citrate (CBC), 7.5 g of talc, and 111.6 g of purified water.

Domperidone (7.5 g), D-mannitol (244.5 g), and crospovidone (15.0 g) were charged into a fluidized bed granulator, and the binder liquid was sprayed to form granules, followed by drying. The resulting dried material was sieved through a sieve having 710 μm openings.

The dry granulated material (227 g) was mixed with magnesium stearate (2.3 g), and the mixture was punched with a rotary tableting machine under the pressure that makes the tablet hardness about 60 N. As a result, orally disintegrating tablets were obtained.

Test Example 5

The tablets obtained in Examples 9 and 10 were measured for tablet hardness in the same manner as in Test Example 1. The tablets were also measured for absorption time, in the same manner as in Test Example 4. The measurement results are presented in Table 6.

TABLE 6

|  | Example 9 | Example 10 |
|---|---|---|
| Domperidone | 5.0 | 5 |
| D-mannitol | 165.5 | 163 |
| Eudragit EPO | 10.0 | — |
| Stearic acid | 1.5 | — |
| Sodium lauryl sulfate | 1.0 | — |
| Eudragit L100 | — | 10 |
| Triethyl citrate | — | 5 |
| Talc | 5.0 | 5 |
| Crospovidone | 10.0 | 10 |
| Magnesium stearate | 2.0 | 2 |
| Total (mg/tab) | 200 | 200 |
| Tablet hardness | 80N | 56N |
| Absorption Time | 34 sec | 24 sec |

Example 11

A binder liquid was obtained by mixing 150 g of a xanthine derivative (INN: Rolofylline (p-INN); 1,3-dipropyl-8-(tricyclo[3.3.1.03,7]non-3-yl)-1H-purine-2,6(3H,7H)-dione) represented by the following formula (I)

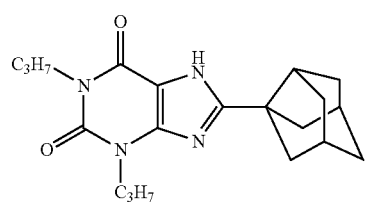

(I)

with 450 g of JPE methacrylic acid copolymer L, and 3,500 g of an ethanol/methylene chloride mixture (weight ratio 1:1).

Lactose (Pharmatose 200 M; DMV; 4,350 g) was charged into a fluidized bed granulator, and the binder liquid was sprayed to form granules, followed by drying. The resulting dry granulated material was sieved through a wire sieve having 710 μm openings.

The granulated material (990 g) was mixed with magnesium stearate (10 g). The mixture (87.8 g) was mixed with 7.2 g of lactose (Tablettose 80; Meggle) and 5.0 g of crospovidone, and the mixture was punched with a rotary tableting machine under the pressure that makes the tablet hardness about 60 N. As a result, orally disintegrating tablets were obtained.

Test Example 6

The tablets obtained in Example 11 were measured for tablet hardness in the same manner as in Test Example 1. The tablets were also measured for disintegration time by performing the disintegration test described in JP 15. The measurement results are presented in Table 7.

As is clear from Table 7, it was possible to obtain orally disintegrating tablets having excellent hardness and disintegration time, even though the tablets contained the poorly soluble drug dissolved in the binder liquid.

TABLE 7

|  | Example 11 |
| --- | --- |
| Xanthine derivative | 5 |
| Eudragit L100 | 15.01 |
| Lactose (Pharmatose 200 M) | 145.13 |
| Magnesium stearate | 1.67 |
| Lactose (Tablettose 80) | 13.68 |
| Crospovidone | 9.5 |
| Total (mg/tab) | 190 |
| Tablet hardness | 63N |
| Disintegration time (Disintegration test in JP 15) | 8 sec |

INDUSTRIAL APPLICABILITY

The present invention can provide an orally disintegrating tablet having desirable oral disintegrability and excellent tablet hardness.

The invention claimed is:

1. An orally disintegrating tablet formed by a process comprising:
    contacting a composition comprising at least one diluent selected from D-mannitol, lactose, trehalose, xylitol, maltitol, and erythritol; a drug; and a disintegrant; with
    a binder liquid comprising at least one binder selected from methacrylic acid-ethyl acrylate copolymer and ethyl acrylate-methyl methacrylate copolymer,
    wherein the weight ratio of the diluent to the binder is 100:1 to 4:1.

2. The orally disintegrating tablet according to claim 1, wherein the binder liquid contains at least one binder selected from methacrylic acid copolymer LD and a copolymer resin of methacrylic acid and ethyl acrylate in methacrylic acid copolymer LD; a copolymer resin of ethyl acrylate and methyl methacrylate in ethyl acrylate-methyl methacrylate copolymer dispersion; and aminoacrylmethacrylate copolymer E.

3. The orally disintegrating tablet according to claim 1, wherein the disintegrant is at least one disintegrant selected from crospovidone, low-substituted hydroxypropylcellulose, crosscarmellose sodium, and starch.

4. The orally disintegrating tablet according to claim 1, wherein the orally disintegrating tablet has a tablet hardness of 40 to 100 N.

5. The orally disintegrating tablet according to claim 1, further comprising a water-soluble film coating layer on a tablet surface.

6. A process for producing an orally disintegrating tablet that contains at least one diluent selected from D-mannitol, lactose, trehalose, xylitol, maltitol, and erythritol; a drug; and a disintegrant,
    the process comprising steps of:
    adding a binder liquid to the diluent and performing wet granulation, the binder liquid containing at least one binder selected from methacrylic acid-ethyl acrylate copolymer and ethyl acrylate-methyl methacrylate copolymer; and
    tableting the granulated material,
    wherein the weight ratio of the diluent to the binder in the wet granulation step is 100:1 to 4:1.

7. The process according to claim 6, wherein the binder liquid is at least one binder liquid selected from:
    a methacrylic acid copolymer LD and/or a ethyl acrylate-methyl methacrylate copolymer dispersion.

8. The process according to claim 6, wherein the wet granulation is fluidized bed granulation.

9. The process according to claim 6, wherein the disintegrant is at least one disintegrant selected from crospovidone, low-substituted hydroxypropylcellulose, crosscarmellose sodium, and starch.

10. The process according to claim 6, wherein the punch pressure in the tableting step produces a tablet hardness of 40 to 100 N.

11. The process according to claim 6, further comprising a step of coating a water-soluble film on the tablet obtained in the tableting step.

* * * * *